US00PP23249P3

(12) United States Plant Patent
Uebelhart

(10) Patent No.: US PP23,249 P3
(45) Date of Patent: Dec. 11, 2012

(54) ***PHYSALIS* PLANT NAMED 'QUEEN'**

(50) Latin Name: *Physalis alkekengi*
Varietal Denomination: Queen

(75) Inventor: Georg Uebelhart, Schwarmstedt (DE)

(73) Assignee: Amazing Breeders Company B.V., Aalsmeer (NL)

( * ) Notice: Subject to any disclaimer, the term of this patent is extended or adjusted under 35 U.S.C. 154(b) by 155 days.

(21) Appl. No.: 12/925,425

(22) Filed: Oct. 21, 2010

(65) Prior Publication Data

US 2012/0102603 P1 Apr. 26, 2012

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — Jondle & Associates, P.C.

(57) ABSTRACT

This invention relates to a new and distinct variety of *Physalis* plant named 'Queen'. The new variety is primarily characterized by an upright, very vigorous growth habit and bright orange husks, is disclosed

.

1 Drawing Sheet

Genus and species: *Physalis alkekengi.*
Variety denomination: 'Queen'.

BACKGROUND OF THE NEW PLANT

The present invention relates to a new and distinct *Physalis* variety designated 'Queen' and botanically known as *Physalis alkekengi*. This new *Physalis* variety was discovered in Toggraben, Germany in September 2007 and originated from an open pollination between the proprietary female parent '06-31' (unpatented) and an un-named *Physalis* plant. The original seedling of the new variety was first asexually propagated by vegetative cuttings in Boijl and Aalsmeer, The Netherlands in 2008.

'Queen' was subsequently asexually propagated and underwent further testing in Boijl and Aalsmeer, The Netherlands for two years. The present invention has been found to retain its distinctive characteristics through successive asexual propagations via stolons and tissue culture.

Plant Breeder's Rights for this variety have not been applied for. 'Queen' has not been made publicly available or sold more than one year prior to the filing date of this application.

DESCRIPTION OF THE PHOTOGRAPH

The accompanying color photograph shows the overall plant habit of a 6-month old plant. The colors shown are as true as can be reasonably obtained by conventional photographic procedures.

DESCRIPTION OF THE NEW VARIETY

The following detailed descriptions set forth the distinctive characteristics of 'Queen'. The data which define these characteristics is based on observations taken in Boijl and Aalsmeer, The Netherlands in September 2010. This description is in accordance with UPOV terminology. Color designations, color descriptions, and other phenotypical descriptions may deviate from the stated values and descriptions depending upon variation in environmental, seasonal, climatic, and cultural conditions. 'Queen' has not been observed under all possible environmental conditions. The botanical description of 'Queen' was taken from 6 month old plants. Color terminology follows The Royal Horticultural Society Colour Chart, London (R.H.S.) (2001).

DETAILED BOTANICAL DESCRIPTION OF THE PLANT

Classification:
- *Species.*—*Physalis alkekengi.*
- *Common name.*—*Physalis.*
- *Denomination.*—'Queen'.

Plant:
- *Height (cm).*—40.0 cm.
- *Diameter (cm).*—30.0 cm.
- *Habit and shape.*—Upright.
- *Vigor.*—Very vigorous.

Shoot:
- *Attitude of one year old shoot.*—40.0 cm.
- *Curvature of one year old shoot.*—Straight.
- *Number of basal shoots per plant.*—30.
- *Prickles.*—Absent.
- *Color.*—RHS 147C.

Leaves:
- *Length, mature (cm).*—8.0 cm.
- *Width, mature (cm).*—5.0 cm.
- *Apex.*—Acute.
- *Base.*—Obtuse.
- *Margin.*—Entire.
- *Shape.*—Deltoid/aristate.
- *Color, both immature and mature.*—Upper surface: RHS 146A. Lower surface: RHS 146B.
- *Texture.*—Smooth.
- *Anthocyanin.*—Absent.
- *Angle of base of blade with petiole.*—Obtuse.
- *Glossiness of both leaf surfaces.*—Weak.
- *Petiole.*—Length (cm): 4.0 cm. Diameter (mm): 4.0 mm. Pubescence: Absent. Color: RHS 146A.

Flower:

*Predominant number of flowers per plant*.—Greater than 50.

*Time of flowering* (*from first to last flower*).—July.

*Sepal*.—Shape: Ovate/rounded and fused. Base: Fused. Length: 5.0 cm. Width: 3.0 cm. Number of sepals per flower: 5. Color (both upper and lower surfaces): RHS 30A.

Fruit:

*Length*.—1.0 cm.

*Width*.—1.0 cm.

*Weight, per individual fruit*.—10 g.

*Relative fruit size*.—Small.

*Predominant fruit shape*.—Round.

*Color*.—RHS 44B.

*Evenness of fruit color*.—Even.

*Pubescence*.—Absent.

*Veining*.—Strong.

*Fruit glossiness*.—High.

*Firmness of flesh*.—Firm.

*Color of flesh*.—RHS 44B.

*Evenness of flesh color*.—Even.

*Peduncle*.—Length (cm): 3 cm. Diameter (cm): 1 mm. Color: RHS 146A. Pubescence: absent.

Disease and insect resistance: No particular resistance observed.

COMPARISON WITH PARENTAL AND COMMERCIAL VARIETIES

*Physalis* 'Queen' cannot be compared to the female parent '06-31', because plants of '06-31' are no longer available.

*Physalis* 'Queen' differs from the commercial variety 'Jumbo' (EUCPVR 10698) in that 'Queen' has a plant height of 40.0 cm and a leaf length of 8.0 cm, whereas 'Jumbo' has a plant height of 60.0 cm and a leaf length of 7.0 cm.

I claim:

1. A new and distinct variety of *Physalis* plant as described and shown herein.

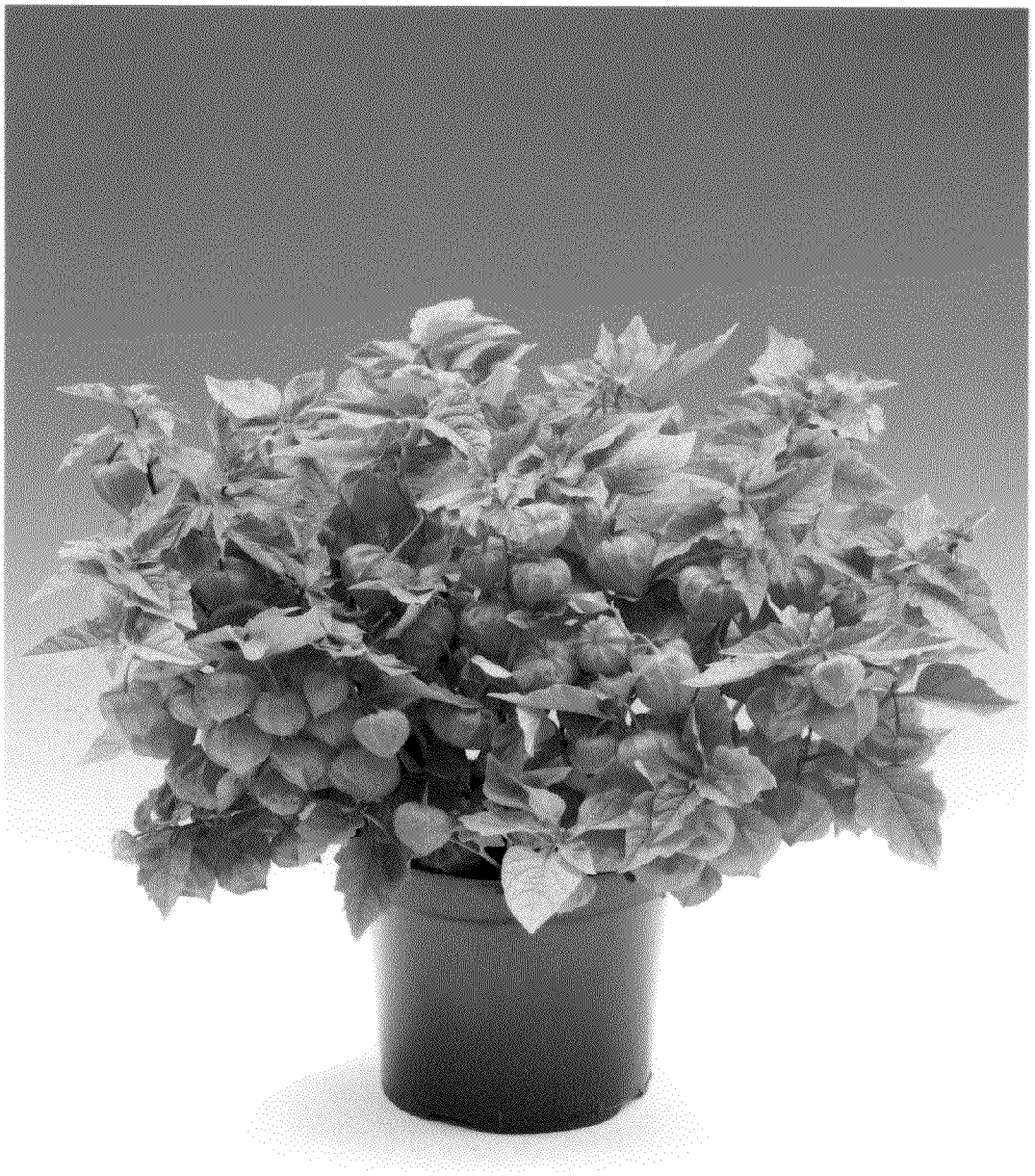

* * * * *